United States Patent [19]

Heinsohn

[11] Patent Number: 5,187,307

[45] Date of Patent: Feb. 16, 1993

[54] SELECTIVITY IN THE OXIDATIVE DEHYDROGENATION OF ALKYL GLYCOLATE

[75] Inventor: George E. Heinsohn, Elkton, Md.

[73] Assignee: E. I. Du Pont de Nemours and Company, Wilmington, Del.

[21] Appl. No.: 602,343

[22] Filed: Oct. 23, 1990

Related U.S. Application Data

[63] Continuation-in-part of Ser. No. 417,652, Oct. 4, 1989, abandoned.

[51] Int. Cl.$^5$ .................... C07C 67/313; C07C 69/67
[52] U.S. Cl. .................................................. 560/177
[58] Field of Search ........................................ 560/177

[56] References Cited

U.S. PATENT DOCUMENTS 4,340,748  7/1982  Baltes et al. .......................... 560/177
4,820,385  4/1989  Cova et al. .......................... 560/177

Primary Examiner—Arthur C. Prescott
Assistant Examiner—V. Garner
Attorney, Agent, or Firm—Charles E. Krukiel

[57] ABSTRACT

In the catalyzed gas phase oxidative dehydrogenation of alkyl glycolate with an oxygen source in the presence of a metallic silver catalyst, the selectivity of from 500 to about 5000 ppm the reaction is increased at high conversion rates by the addition of methylene chloride to the reactants.

9 Claims, No Drawings

SELECTIVITY IN THE OXIDATIVE DEHYDROGENATION OF ALKYL GLYCOLATE

This application is a continuation-in-part of application Ser. No. 07/417,652 filed Oct. 4, 1989 now abandoned.

FIELD OF THE INVENTION

This invention relates in general to the production of alkyl glyoxylate and, more particularly, to an improved method for the catalytic gas phase oxidative dehydrogenation of alkyl glycolate, in which there is an increase in the selectivity for alkyl glyoxylate.

BACKGROUND OF THE INVENTION

In the catalytic gas phase oxidative dehydrogenation of alkyl glycolate using a silver catalyst, the higher the catalyst temperature employed, the lower the selectivity for alkyl glyoxylate. Because of the potentially low selectivity for alkyl glyoxylate at high temperatures, i.e., above about 700° C., prior art processes kept the reaction temperature low, i.e., below about 400° C., by, among other techniques, adding diluents. For example, U.S. Pat. No. 4,340,748 discloses a process in which glyoxylic esters are produced in high yields by the catalytic oxidative dehydrogenation of glycolic acid esters in the gaseous phase in the presence of a silver catalyst. By using 40 to 60 moles of a carrier gas per mole of the glycolic acid ester, the temperature of the reactor can be maintained at 200° to 400° C. Catalyst productivity measured as space time yield is, however, low due to the high degree of dilution. U.S. Pat. No. 4,340,748 discloses carrying out the reaction with an effective amount of a catalyst promoter and an inert substance (water, chlorinated hydrocarbons, etc.) to increase selectivity of the reaction. Chloroform is the only chlorinated hydrocarbon disclosed, and in Example 11 it is used in relatively large quantities, i.e., about 0.36 moles of chloroform per mole of alkyl glycolate, equivalent to 330,000 parts $CHCl_3$ per million parts alkyl glycolate. The reaction in Example 11 has a catalyst carrier containing several metal catalysts, including silver, together with a metal catalyst promoter. The process disclosed in U.S. Pat. No. 4,340,748 may be unsuitable in certain instances where a pure silver catalyst is used, because the use of large quantities of a chlorinated hydrocarbon are known to poison or otherwise deleteriously affect the catalytic activity of silver. The process also has the disadvantage of requiring the use of an expensive catalyst promoter.

European Patent No. 149,439 recommends against using diluents when it is desired to achieve high selectivity. Instead, European Patent 149,439 minimizes the residence time in the reactor by passing the reactant stream through a catalyst bed at a very high linear velocity. In this way, the time is minimized that the reactant stream is subjected to high temperatures and catalytically active areas. Since diluents are not used, the reactor temperature increases to 400°-600° C. To minimize side reactions, extremely high gas velocities and correspondingly short contact times are employed so that the conversion of the alkyl glycolate is limited to less than 70 percent. This process has the disadvantage that the short contact time results in a relatively low rate of conversion of the alkyl glycolate which, in turn, makes it difficult to isolate the desired product from unreacted starting materials.

It is well known to use additives to increase the selectivity in several silver-catalyzed oxidation reactions. One theory advanced is that the additive partially poisons the catalyst, thereby minimizing side reactions. The oxidation of ethylene is one such area where the principle of catalyst poisoning to increase selectivity has been used. Many additives have been disclosed in the epoxide literature that increase the selectivity of the reaction [Kirk-Othmer Encyclopedia of Chemical Technology (3rd edition, Volume 9, pp. 441-449) which is incorporated herein by reference]. The use of catalyst inhibitors to suppress undesired side reactions is also discussed in Kirk-Othmer. Catalyst inhibitors include aromatic hydrocarbons, amines, organometallic compounds and alkyl halides.

It is well known that adsorption of oxygen on metallic silver can proceed by several different pathways depending upon many variables including temperature, partial pressure of oxygen, and the detailed structure of the silver surface. It has been theorized that different forms of adsorbed oxygen react with organic substrates by different mechanisms to produce different products. For example, it has been suggested in Kirk-Othmer, 3rd edition, Volume 9, pp. 441, that a monoatomic oxygen species adsorbed on silver reacts with ethylene to form $CO_2$ while a co-formed diatomic oxygen species reacts with ethylene to form ethylene oxide. These reactions are shown as follows:

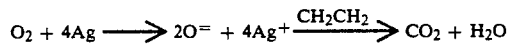

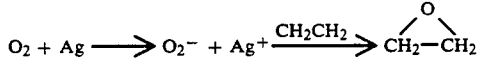

In certain silver-catalyzed oxidations of ethylene, increased selectivity for ethylene oxide formation is achieved by adding to the catalyst or to the feed stream certain materials which are believed to alter the ratios of the various adsorbed oxygen species. Catalysis Review for Science and Engineering, 22(2), p. 224 (1980), discloses that other additives, such as alkali and alkaline earth metals, chlorine, sulfur, selenium, tellurium, phosphorous, and certain halogenated organics have been found to increase the selectivity.

The choice of a suitable additive to enhance the selectivity is dependent upon the detailed nature of the chemical process. In the oxidative dehydrogenation of methanol to formaldehyde in the presence of a silver catalyst, certain phosphorous compounds have been found to enhance the selectivity as in the ethylene oxide process. However, other additives which are beneficial to the ethylene oxidation, such as sulfur, alkali metals and halogenated hydrocarbons, have been found to be detrimental in the formaldehyde process. Consequently, techniques which are successful in one silver-catalyzed oxidative dehydrogenation cannot be extrapolated to another chemical system. In this connection, although the ethylene oxide technology may explain the mechanism in which oxygen is absorbed onto a silver catalyst, it cannot predict which substances will promote the oxidation of alkyl glycolate. In any particular chemical reaction, there are factors which are as important as the mode in which the oxygen is absorbed on the catalyst.

It is, therefore, desirable to have an economical process for the production of alkyl glyoxylates and provide an additive which will increase the selectivity of the alkyl glyoxylate at high rates of conversion for alkyl glycolate.

OBJECTS OF THE INVENTION

It is a principal object of the present invention to provide an improved process for the production of alkyl glyoxylate which results in economy of operation and increased product yield.

Another object of the invention is to provide an additive which will increase the selectivity of alkyl glyoxylate at high rates of conversion for alkyl glycolate.

Upon further study of the specification and appended claims, further objects and advantages of this invention will become apparent to those skilled in the art.

SUMMARY OF THE INVENTION

An improved process is provided for the production of alkyl glyoxylate by the catalyzed gas phase oxidative dehydrogenation reaction of alkyl glycolate in the presence of an oxygen source and metallic silver catalyst, wherein the reaction is performed without a catalyst promoter in the presence of from about 500 to 5000 ppm of methylene chloride.

In a preferred aspect, the present invention provides an improved process for increasing the selectivity for the alkyl glyoxylate product 10 percent at conversion rates of alkyl glycolate of 90 percent using air, a crystalline silver catalyst, and concentrations of methylene chloride of from about 2000 to 3000 ppm. The methylene chloride can be added directly to the reactor.

More specifically, in a preferred embodiment of the present proces, the methylene chloride is added to the alkyl glycolate before an oxygen source or a carrier gas is added. The reaction can be carried out in two reaction stages in series with intercooling between the reaction stages.

DETAILED DESCRIPTION

It has been discovered that the addition of methylene chloride in the silver-catalyzed gas phase oxidative dehydrogenation of alkyl glycolate can significantly increase the selectivity for alkyl glyoxylate, especially at high rates of conversion of the alkyl glycolate. In the process of the present invention, methylene chloride can be added directly to the reactor without any apparent poisoning or deleterious effect on the metallic silver catalyst. It has been found that even extremely small amounts, i.e., about 500 ppm, of the methylene chloride produce an increase in the selectivity for the alkyl glyoxylate, without reducing the conversion of the alkyl glycolate.

The amount of methylene chloride that can be added to the reaction mixture can range from about 500 to 5000 ppm. It has been found that when 500 ppm or less of methylene chloride is added to the reaction mixture, there is little effect on selectivity. When more than about 3000 ppm of methylene chloride is added, no additional benefits are observed. In a preferred aspect of the present invention, from about 2000 to 3000 ppm, of methylene chloride is added to the reaction mixture. The methylene chloride can be added to the reaction mixture in a variety of ways.

The addition of methylene chloride is believed to partially poison the catalyst so that the formation of the alkyl glyoxylate product is promoted in the same manner as the selectivity of ethylene oxide is increased with the addition of a catalyst inhibitor.

The above-described concentrations of the methylene chloride can be used in the gaseous reaction mixture with the concentrations of an oxygen source and carrier gas described herein.

The alkyl glycolate used as a reactant in the oxidative dehydrogenation reaction can be prepared by the esterification of glycolic acid with an aliphatic alcohol. The aliphatic alcohol can contain from 1 to 6 carbon atoms. Methanol is preferred. Suitable methods to produce alkyl glyoxylate are described in U.S. Pat. No. 4,340,748 and European Patent No. 149,439. The preferred methods to produce alkyl glyoxylate are described in copending patent applications Ser. Nos. 07/417,653 and 07/417,651 G. Heinsohn, "Multi-Stage Process With Adiabatic Reactors for Preparing Alkyl Glyoxylates, and G. Heinsohn, "Process for the Preparation of Alkyl Glyoxylates"], which are incorporated herein by reference. Alkyl glyoxylate is currently used in the synthesis of pharmaceuticals.

The preferred catalyst for the process of the present invention is silver. It is preferred to use an unsupported crystalline silver catalyst, which has the advantage of including a high space time yield and a high selectivity. Preferably, high purity silver, e.g., in the form of 99.9 percent pure crystals, is used. The preferred configuration of the catalyst particles is in a horizontal shallow fixed catalyst bed. The reaction can be carried out in the presence of methylene chloride in two or more reaction stages in series and by providing in the first reaction stage, less than the stoichiometric amount of oxygen theoretically required to completely oxidize all of the alkyl glyoxylate to the corresponding alkyl glycolate, preferably less than about 60 percent. The effluent from the reaction stages preferably is cooled to about 250° C. between stages to provide further temperature control and the product gaseous stream from the last reaction stage is cooled and condensed. In each reaction stage, there is either excess reactant or previously formed alkyl glyoxylate product which, as a result of the intercooling, introduces the reaction mixture to a reactor at a temperature below the desired maximum to provide further heat-absorbing capacity to the system.

It is important that the gaseous mixture fed to the reactor is uniformly and completely mixed in the gaseous state to form a homogenous gaseous stream. Any one of a number of conventional means can be used to accomplish this. One preferred method is to vaporize the alkyl glycolate and methylene chloride in a long vertical tube evaporator to remove any mist left in the mixture. Preferably, the air is preheated and then uniformly mixed with the heated alkyl glycolate and methylene chloride at a temperature high enough to avoid the formation of any mist. Failure to eliminate the mist or entrained liquid may adversely affect the reaction selectivity and life of the catalyst.

The air or other source of oxygen may be preheated in a preheater, preferably to a temperature above the condensation temperature of the alkyl glycolate. The oxygen source is fed directly to the air preheater. When multiple reaction stages are used, it is preferred to use an overall amount of oxygen of from 0.05 to 1.0, more preferably from 0.4 to 0.8, moles of oxygen per mole of alkyl glycolate in the starting gaseous mixture entering the first reaction stage. If the oxygen source is mixed with previously vaporized alkyl glycolate and methylene chloride, it is preferred to preheat the oxygen to a temperature above the condensation point of alkyl glycolate in order to prevent the formation of mist during mixing.

Although no carrier gas need be used, it is preferred to add to the alkyl glycolate and methylene chloride mixture from about 1 to 3 moles of nitrogen per mole of alkyl glycolate, in addition to that present in the incoming air, to aid in vaporization and in temperature control inside the reactor. More nitrogen may optionally be added to control the reactor temperature. It is preferred that the methylene chloride be vaporized with the alkyl glycolate before air is introduced or added with a carrier gas.

The amount of oxygen entering the first stage with alkyl glycolate preferably is no more than about 60 percent of the stoichiometric amount, based on the alkyl glycolate entering the first stage, and is preferably from about 42 to 52 percent.

The gaseous reaction mixture, including the vaporized alkyl glycolate, methylene chloride, oxygen, and optionally nitrogen, either that present in the air used as the source of oxygen alone or in admixture with from about 0 to 5, preferably 1 to 3 molar equivalents additional diluent nitrogen, entering the first reaction stage is preferably at a temperature of about 150° to 300° C. As this gaseous reaction mixture passes through the catalyst bed, resulting in the liberation of heat, the temperature of the reaction mass increases. The mean temperature of the reaction mass in the catalyst bed in the first stage is preferably from about 400°-700° C., more preferably from about 450°-625° C. and in the second and any succeeding stages is preferably from about 400°-700° C., more preferably from about 450°-625° C. The effluent from the first reaction stage contains the alkyl glycolate, methylene chloride, water vapor, alcohol, and nitrogen, if air is used as the source of oxygen or if nitrogen is used as a carrier gas.

Additional oxygen is added to the effluent from the first reaction, preferably after cooling the effluent to below 300° C. The amount of oxygen added to the reaction mixture as it leaves any of the non-final stages is dependent upon the cumulative amount introduced to the preceding stage or stages and upon the total number of reaction stages remaining. Preferably, sufficient oxygen is added at each of these inner stage points so that the total amount of oxygen that has been added to the system, including the amount added to the first reactor, is at least equal to and preferably slightly in excess, e.g., from 100% to 120%, of the stoichiometric requirement of oxygen based on the amount of alkyl glycolate in the feedstream.

For example, when two reaction stages are used, it is preferred to introduce from about 40 to 55 percent of the stoichiometric amount thereof in the second stage, the total amount of oxygen fed to the system ordinarily being at least equal to 100 percent of the stoichiometric amount of oxygen needed to oxidize all of the alkyl glycolate feed.

Since alkyl glyoxylates form oligomers and other side reactions occur at elevated temperatures, it is preferred to rapidly cool the effluent from each of the reaction stages. This prevents undesirable decomposition of the product, as well as providing heat absorbing capacity for temperature control for the second and any succeeding reaction stages. The optional cooling, e.g., in a heat exchanger, between the reaction stages preferably is sufficient to cool the gaseous stream to a temperature below about 300° C., and more preferably to about 150° to 300° C.

If desired, the oxygen or oxygen-containing gases added between stages can be at a temperature sufficiently lower than the reaction effluent to which it is added in order to at least partially effect this interstage cooling. Alternatively or additionally, cooling in conventional heat exchange equipment, such as a standard shell and tube heat exchanger, can be used to cool the reaction mixture to the selected lower temperature before it is introduced into the next succeeding stage.

The absolute pressure of the gas mixture in the reactors, including inert gases, if any, is not critical and can be varied. It is preferred to operate the process at a pressure of from about 0.5 to 2.0 atmospheres.

The range of conversion of alkyl glycolate can be varied over a wide range, depending on the amount of excess oxygen utilized and the temperatures employed in the reaction stages. The selectivity for the alkyl glyoxylate product can also be varied depending upon the concentration of methylene chloride in the starting reactants. It is preferred to employ conditions whereby the conversion rate of the alkyl glycolate ranges from about 50-100 percent, more preferably about 75-95 percent. As the conversion declines below the preferred range, it becomes increasingly expensive to isolate the product. The reaction can be carried out in the presence of an inert gas, preferably nitrogen, which provides additional heat absorbing capacity. As the conversion rate approaches 100 percent, selectivity tends to drop. According to the present invention, the drop in selectivity at high rates of conversion can be offset by the addition of methylene chloride to the reaction mixture.

The effluent from the reactor generated from any of the previously-referenced preparation procedures should be rapidly cooled to minimize product loss. The cooled effluent can then be separated to isolate the alkyl glyoxylate product by the methods described in U.S. Pat. No. 4,502,923 or Australian Patent No. 30007-84.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and, unless otherwise indicated, all parts and percentages are by weight.

EXAMPLES

Examples 1-5

A first tubular reactor (10 millimeters inner diameter and 20 centimeters long) constructed of quartz was charged with 7.0 grams of crystalline silver (20 to 30 Tyler mesh) to form a catalyst bed 2.0 centimeters deep. The reactor tube was fitted with an external heater to raise the temperature of the catalyst bed to 400° C. and initiate the reaction. Internal thermocouples in the bed were used to measure catalyst temperature. 22.5 g/hr (0.25 mole/hr) of methyl glycolate containing methylene chloride as shown in Table 1 was continually vaporized and mixed with 104 cubic centimeters/minute of air at standard temperature and pressure (0.058 moles oxygen/hr) and 125 cubic centimeters/minute of nitrogen. The resultant gas mixture was introduced into the reactor at gradually increasing rates until the entire feed stream reached the rate of 22.5 g/hr. When steady state operation was achieved, the external heater was adjusted to compensate for heat lost by the reactor to the surroundings to simulate adiabatic operation of a large-scale reactor. The internal temperature of the reactor was 530° C. The effluent from the reactor was cooled to 250° C., mixed with 140 cubic centimeters/min of additional air at standard temperature and pressure (0.079 moles oxygen/hr) and introduced into a second quartz reactor identical in configuration and structure to the first reactor. The internal temperature of the second reactor was 560° C. The effluent from the second reactor was analyzed by gas chromatography and found to contain methyl glyoxylate and methyl glycolate as shown in Table 1 below.

EXAMPLE 6

Comparative Example

Example 1 was repeated without the use of a methylene chloride additive. The product stream contained 12.9 g/hr of methyl glyoxylate representing a selectivity of 65% at 90% conversion of methyl glycolate.

TABLE 1

| Ex. No. | $CH_2Cl_2$ (ppm) | Methyl Glycolate (g/hr) | Methyl Glyoxylate (g/hr) | Percent Conversion | Percent Selectivity |
|---|---|---|---|---|---|
| 1 | 250 | 22.5 | 12.9 | 90 | 65 |
| 2 | 500 | 22.5 | 13.3 | 90 | 67 |
| 3 | 2000 | 22.5 | 14.9 | 90 | 76 |
| 4 | 3000 | 22.5 | 15.3 | 90 | 78 |
| 5 | 5000 | 22.5 | 15.3 | 90 | 78 |
| 6 | 0 | 22.5 | 12.9 | 90 | 65 |

The preceding examples can be repeated with similar success by substituting the generically or specifically described reactants and/or operating conditions of this invention for those used in the preceding examples.

EXAMPLE 7

Comparative Example

A tubular reactor (10 mm inner diameter and 20 mm long) was charged with 7.0 g of crystalline silver (20 to 30 Tyler mesh) to form a catalyst bed 2 cm deep. The reactor tube was fitted with an external heater to raise the temperature of the catalyst bed to 420° C. and initiate the reaction. Methyl glycolate (22.5 g/hr, 0.25 mole/hr) was continuously vaporized and mixed with 104 cc/min of air at standard temperature and pressure (0.058 mole oxygen/hr) and 125 cc/min nitrogen. The resulting gas mixture was introduced into the reactor at gradually increasing rates until the entire feed stream was flowing over the heated catalyst. An exothermic reaction ensued causing the temperature of the catalyst to rise to 495°–500° C. The reactor reached a steady state in about 1 hr and was allowed to run for an additional 2.5 hr during which time samples were periodically collected for analysis which demonstrated that conversion of methyl glycolate was 45% and selectivity for methyl glyoxylate was 85%. At this point, the pure methyl glycolate feed was replaced by methyl glycolate containing 66,400 ppm of chloroform. From the volume of the connecting lines and the feed rate, it was estimated that it would take 30 min for the chloroform to reach the silver catalyst. Samples were withdrawn periodically for analysis by gas chromatography. Table 2 summarizes the results expressed as area percentages of methyl glyoxylate (MGX) and methyl glycolate (MGL) in the chromatogram since the time interval between samples was too short for accurate determination of conversion and selectivity. The time is reported in minutes after addition of chloroform to the feed.

TABLE 2

| Time | Temperature | % MGX | % MGL |
|---|---|---|---|
| 0 | 502° C. | 29.99 | 58.71 |
| 30 | 501° C. | 29.16 | 56.51 |
| 45 | 464° C. | 16.82 | 68.88 |
| 60 | 430° C. | — | — |
| 75 | 410° C. | 6.85 | 82.08 |
| 100 | 410° C. | 3.44 | 88.18 |

During the final 30 min period, a sample was collected, weighed and analyzed, showing that conversion averaged 11.8% and selectivity averaged 35% over this interval.

EXAMPLE 8

Comparative Example

In the manner described in Example 7, the reactor was equilibrated using pure methyl glycolate. The catalyst bed stabilized at 490°–495° C. and samples collected over a 2.5 hr period showed that conversion averaged 45% and selectivity averaged 86%. The pure MGL was then replaced by MGL containing 30,000 ppm of methylene chloride. After about 30 min, the temperature of the catalyst bed began to drop. Additional energy was supplied to the external heater in an effort to maintain the catalyst at 490° C. and this procedure periodically repeated throughout the run. The run was terminated when the catalyst bed temperature dropped below 450° C. even with the heater at maximum output. Samples were periodically collected and analyzed giving the results summarized in Table 3. Time is reported in minutes after addition of methylene chloride to the feed.

TABLE 3

| Time | % Selectivity | % Conversion |
|---|---|---|
| 0 | 84 | 47 |
| 30 | 82 | 43 |
| 60 | 69 | 35 |
| 90 | 64 | 33 |
| 120 | 53 | 33 |
| 150 | 48 | 33 |
| 180 | 45 | 32 |
| 210 | 47 | 29 |

Example 7 shows that when chloroform is present in the alkyl glyoxylate feed at the level employed in U.S. Pat. No. 4,340,478 [Baltes et al., i.e., 66,400 ppm], a pure silver catalyst is rapidly deactivated and is essentially inert after 30–45 minutes' exposure. Baltes et al. reported high conversion and selectivity over a 2 hr period, and it may be concluded that the silver present in the catalyst of Baltes et al. made little if any contribution toward that result. Furthermore, Example 7 of U.S. Pat. No. 4,340,748 demonstrates that similar results may be achieved when vanadium is the only catalyst present.

Example 8 shows that even at modest levels (less than ½ the dosage rate employed by Baltes et al.), methylene chloride exerts a strong and deleterious effect on both conversion and selectivity when silver is employed as catalyst. Only by ever-increasing the energy input could even a diminished level of activity be maintained.

There is a fundamental difference between a pure silver catalyst and a complex catalyst of the type employed by Baltes et al. in that pure silver is rendered inert by modest levels of chlorine (introduced as methylene chloride or as chloroform) while a complex catalyst is not. Given that modest levels of methylene chloride (3% in Example 8) exert a strong deleterious effect on pure silver, it is unexpected that, in contrast to the conclusions which could be drawn from the prior art, very low levels of methylene chloride (500-5000 ppm) enhance selectivity with no apparent penalty in conversion, thereby improving the yield of product.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the production of alkyl glyoxylate by the catalyzed gas phase oxidative dehydrogenation reaction of alkyl glycolates with a source of oxygen which is gaseous oxygen or air in the presence of a metallic silver catalyst, the improvement wherein the reaction is conducted in the presence of from about 500 ppm to about 5000 ppm of methylene chloride and in the absence of a catalyst promoter.

2. The process of claim 1, wherein the catalyst is crystalline silver.

3. The process of claim 1, wherein the methylene chloride is vaporized with the alkyl glycolate before being mixed with an oxygen source or a carrier gas.

4. The process of claim 1, wherein the oxygen source is air.

5. The process of claim 3, wherein the reaction is conducted in the presence of a carrier gas.

6. The process of claim 1, wherein the alkyl moiety of the alkyl glycolate and alkyl glyoxylate contains from 1 to 6 carbon atoms.

7. The process of claim 1, wherein the alkyl glyoxylate is methyl glyoxylate.

8. The process of claim 1, wherein the reaction is conducted in the presence of from about 2000 to 3000 ppm of methylene chloride.

9. The process of claim 1, wherein the oxygen source is air, wherein the gas phase contains from about 1-3 moles of additional nitrogen per mole of alkyl glycolate; wherein the reaction is carried out in two reaction stages in series, the temperature of the first reaction stage being from about 450° to 650° C.; wherein effluent from the first reaction stage is cooled to about 250° C. before being introduced into the second reaction stage; and wherein a stoichiometrically deficient amount of oxygen is used in the first reaction stage and additional oxygen is introduced in the second reaction stage so that the total amount of oxygen that has been added to the system is at least equal to the stoichiometric requirement of oxygen based on the amount of alkyl glycolate in the process feedstream.

* * * * *